United States Patent [19]

Eltoukhy et al.

[11] Patent Number: 5,074,983
[45] Date of Patent: Dec. 24, 1991

[54] THIN FILM TESTING METHOD

[75] Inventors: Atef H. Eltoukhy, Saratoga; Yassin Mehmandoust, Berkeley, both of Calif.

[73] Assignee: HMT Technology Corporation, Fremont, Calif.

[21] Appl. No.: 341,936

[22] Filed: Apr. 21, 1989

[51] Int. Cl.$^5$ .......................... C23C 14/34; G01N 3/56
[52] U.S. Cl. .......................... 204/192.13; 204/192.16; 73/7; 73/150 R
[58] Field of Search .................. 73/7, 150 R; 204/192.15, 192.16, 192.2, 192.13

[56] References Cited

U.S. PATENT DOCUMENTS

| | | | |
|---|---|---|---|
| 4,737,419 | 4/1988 | Hilden et al. | 204/192.16 X |
| 4,774,130 | 9/1988 | Endo et al. | 204/192.2 X |
| 4,778,582 | 10/1988 | Howard | 204/192.15 |
| 4,869,797 | 9/1989 | Nagao et al. | 204/192.16 |
| 4,898,774 | 2/1990 | Yamashita et al. | 204/192.2 X |

FOREIGN PATENT DOCUMENTS

61-117727 6/1986 Japan ........................... 204/192.15

Primary Examiner—Nam X. Nguyen
Attorney, Agent, or Firm—Peter J. Dehlinger

[57] ABSTRACT

A method of evaluating the start/stop lifetime of a thin-film magnetic medium having an overcoat formed by sputtering a carbon-containing overcoat on a magnetic-film substrate. Resistance to erosion of the medium is evaluated by the time required to wear away the overcoat during a high-speed abrasion treatment. Lubricity is measured either in terms of the coefficient of friction of the disc, or in terms or surface hydrophobicity, as gauged by one of a number of measurable surface properties. The method allows for rapid assessment of disc wear properties, and can be used to optimize sputtering conditions required to achieve selected hardness and lubricity properties in a disc overcoat.

20 Claims, 4 Drawing Sheets

THIN FILM TESTING METHOD

1. FIELD OF THE INVENTION

The present invention relates to a method of testing wear-related characteristics of a magnetic thin-film disc having a carbon overcoat, and the use of the method for optimizing overcoat properties.

2. REFERENCES

Craig, S., et al, Thin Solid Films, 97:345 (1982).

Kobayashi, K., et al., Thin Solid Films, 158:233 (1988).

Natarajan, V., et al., J Vac Sci Technology, A3(3):681 (1985).

Research Disclosure RD269061, K. Mason Publications, Ltd., England (1986).

Tsai, H-C., et al., J Vac Sci Technol, A5(6):3287 (1987).

Yolamanchi, R. S., et al., Thin Solid Films, 164:103 (1988).

3. BACKGROUND OF THE INVENTION

Magnetic overcoats are commonly formed on substrates, such as magnetic thin-film discs employed for recording data. The thickness of the overcoat is typically between about 200-500 Å and preferably about 300 Å. Greater thickness of the overcoat, and thus greater distance between the thin-film magnetic storage layer and the read/write head, tends to degrade disc resolution and storage density.

The carbon overcoat functions to protect the underlying magnetic layer from damage and wear caused by repeated contact between the disc and the read-write used in accessing the disc. For this reason, the graphite overcoat is ideally formed to have a high degree of hardness or erosion-resistance.

In addition, the graphite overcoat is intended to provide lubricating surface properties, to minimize drag on the head and wear on the disc during prolonged head/disc contact. The overcoat therefore ideally provides a low-friction surface. The lubricity of a hard carbon overcoat on a disc may be enhanced by covering the overcoat with a thin liquid layer of a stable fluid material, such as a fluorocarbon. The optimum friction reduction may be achieved with a liquid layer of fluorocarbon of about 15-30 Å. With a thicker liquid layer, the head may tend to "blot" the liquid layer, producing greater drag between the head and disc with a resultant reduction in the operating lifetime for the disc.

A variety of methods have been used heretofore for forming carbon overcoats on a thin-film magnetic disc (Tsai). In one method, known as RF plasma or glow discharge, an RF source is used to decompose an hydrocarbon gas, producing a carbonaceous plasma whose carbon particles are deposited on a thin-film substrate to form the carbon overcoat (e.g., Natarajan; Yolamanchi; and Kobayashi). The RF discharge method is relatively slow, and deposition rates and plasma composition are somewhat difficult to control.

Another method which has been used for producing a carbon overcoat involves carbon deposition by DC sputtering, typically DC magnetron sputtering, in which the ionized gases are directed onto the target by magnetic fields established in the sputtering device. Typically in this method, a graphite substrate is sputtered onto a thin-layer film substrate in a low-pressure argon gas until an overcoat of the desired thickness is reached.

The resulting carbon overcoat has a predominantly graphitic structure with "islands" of diamond-like crystalline clusters with dimensions on the order of about 20 Å. It is, of course, the diamond-like clusters which impart the hardness properties to the overlayer. Although the overcoat formed in this manner has adequate hardness properties, it would be desirable to increase the lubricity of the layer as well, particularly the lubricity of the overcoat after initial wear. Experiments conducted in support of the present invention indicate that carbon overcoats formed by DC magnetron sputtering in a pure argon atmosphere tend to show a substantial loss of lubricity as the overcoat is worn, in turn, causing greater wear on the overcoat. As a result, mechanical stress in the system wearing away of the disc overcoat are both accelerated.

The need for increased lubricity is especially great in the inner diameter region of the disc, where the fluorocarbon liquid coating applied to the overcoat becomes depleted over time due to migration of the liquid material under centrifugal effects, and particularly, in the inner-diameter region which is dedicated to start-stop head contact, where repeated contact with the head further depletes the liquid layer.

Various modifications of DC sputtering for use in producing carbon overcoats have been proposed. One modification, for example, is to form the overcoat by DC sputtering of a carbon target in the presence of methane or a mixture of argon and methane (RD 269061; Craig). This approach has the potential for increasing the lubricity of carbon overcoat films, as has been verified by experiments conducted in support of the present invention. However, experiments conducted in support of the present invention indicate that merely adding hydrocarbon gas to the sputtering chamber increases lubricity, but also reduces hardness, i.e., resistance to wear.

Heretofore, the development of methods for producing durable, high-lubricity overcoats for thin-film media has been hampered by slow and/or inaccurate disc testing procedures. Disc hardness is measured, according to the prior art, by a static or dynamic (moving disc) scratch test in which the depth of scratch or indentation (at a given scratch pressure applied to the disc), provides a measure of hardness. This test is difficult to quantitate, and does not necessarily correlate well with the expected start/stop lifetime of a disc.

The lubricity properties of carbon-overcoat discs are generally measured in terms of static or dynamic (rotating disc) coefficients of friction. This is done by a standard drag test in which the drag produced by contact of a read/write head with a disc is determined. One important property of a disc which is required for good long-term disc and drive performance is that the disc retain a relatively low coefficient of friction after many start/stop cycles or contacts with a read/write head. For example, a drive manufacturer may require that the disc have an initial coefficient of static friction no greater than 0.3, and a coefficient of static friction of no greater than 0.6 after 20,000 start/stop cycles. This disc specification indicates that the disc can tolerate at least 20,000 start/stop cycles without showing high friction characteristics which would interfere with read/write operations.

In fact, the above start/stop lifetime test, in which the coefficient of friction is measured before and after a large number of start/stop cycles, has heretofore been the only reliable measure of start/stop lifetime of a disc.

An obvious limitation of this test is the length of time required, as well as the wear on the testing machinery. More importantly, the results of the test do not indicate how changes in hardness and/or lubricity, as measured by prior art methods, would lead to greater durability, or more generally, how the hardness and lubricity properties of an overcoat can be varied to produce desired durability and low-friction properties in a disc.

4. SUMMARY OF THE INVENTION

It is therefore one general object of the invention to provide a method of testing thin-film media for surface hardness and lubricity characteristics which substantially overcomes limitations associated with prior art testing methods.

It is a related object of the invention to provide such a method which can be used in conjunction with carbon overcoat sputtering methods to achieve desired hardness and lubricity characteristics in an overcoat.

In one aspect, the invention includes a method of evaluating the expected start-stop lifetime of a thin-film magnetic medium formed by sputtering a carbon-containing overcoat on a thin-film substrate. The method includes the steps of:

(a) measuring the resistance to erosion of the overcoat by (a) placing against the disc, a roller covered with an abrasive tape and oriented to rotate with disc rotation, (b) rotating the disc, and (c) with the roller pressed against the overcoat, measuring the overcoat removal time required to remove a selected portion of the overcoat;

(b) measuring the lubricity of the overcoat; and (c) correlating the measured resistance to erosion and lubricity with the same parameters in discs with known start-stop lifetimes.

In one preferred method, the resistance to erosion is measured by rotating the disc at a speed of about 1,800 rpm, under conditions in which the hardest disc overcoats can be substantially worn away within at most about 15 minutes.

The lubricity is measured, in accordance with one embodiment of the invention, by measuring the dynamic coefficient of friction before and after a given period of head drag on an unlubricated overcoat.

In another general embodiment, the lubricity is measured in terms of the hydrophobicity of the disc. This property may be determined from the angle from horizontal at which of bead of water placed on the disc begins to glide on the disc. Alternatively hydrophobicity can be measured from the ratio of exposed carbon-:oxygen-containing groups on the overcoat surface. In addition, high reflectivity and/or a bright gold overcoat color may characterize an overcoat having the desired hydrophobic properties.

In another aspect, the invention includes a method for use in establishing optimal operating parameters for forming a graphite overcoat on a thin-film magnetic substrate by DC magnetron sputtering of a carbon substrate in a low-pressure argon/hydrocarbon atmosphere. The method includes the steps of:

(a) measuring resistance to erosion of the graphite overcoat, (b) measuring the lubricity of the graphite overcoat, and (c) based on the measured values of hardness and lubricity, adjusting the ratio of argon:hydrocarbon in the sputtering atmosphere to selectively vary the lubricity of the overcoat, and adjusting the sputtering voltage and gas pressure in the sputtering chamber, to produce a desired degree of hardness at the selected lubricity.

These and other objects and features of the invention will become more fully apparent when the following detailed description of the invention is read in conjunction with the accompanying drawings.

DETAILED DESCRIPTION OF THE INVENTION

The testing method of the invention is described in Section I below. Section II describes a sputtering method which is used in conjunction with the testing method to achieve desired overcoat hardness and lubricity properties in a carbon overcoat. Properties of a carbon overcoat formed in accordance with the testing and sputtering method are detailed in Section III.

I. Testing Carbon Overcoat Surface Properties

Figures 1, 2:
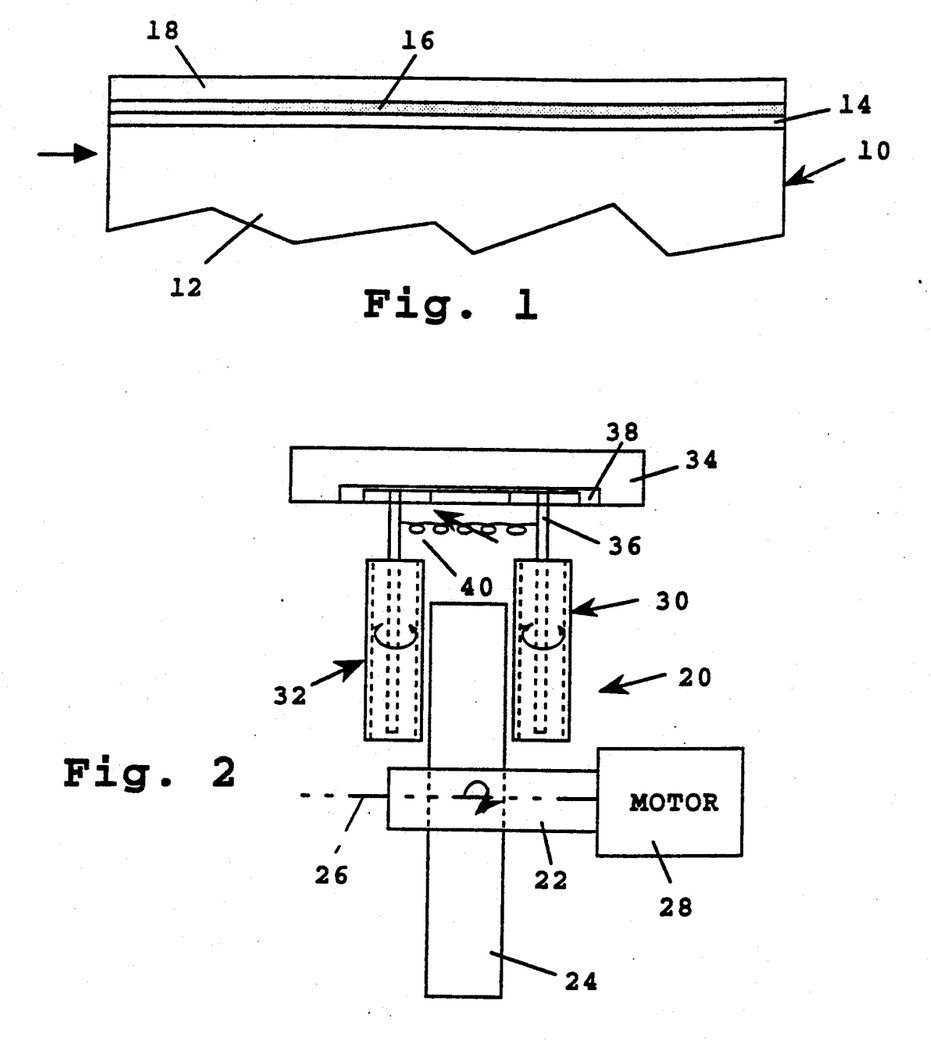
FIG. 1 is a sectional view of a thin-film magnetic disc having a carbon overcoat whose properties are to be tested and optimized in accordance with the present invention.
FIG. 2 is a schematic representation of a device for rapidly measuring carbon overcoat resistance to erosion, in accordance with the invention.

FIG. 1 is a fragmentary portion of a thin-film medium or disc 10 constructed according to the method described in Section II, and whose resistance to erosion, lubricity, and start/stop lifetime characteristics are to be tested, in accordance with the present invention.

The disk generally includes a rigid substrate 12, and forming successive thin-film layers over the substrate, a crystalline underlayer 14, a magnetic thin film layer 16, and a carbon overcoat 18, preferably about 200–400 Å. The magnetic thin film layer formed on the substrate is also referred to herein as a thin-film substrate. It is understood that FIG. 1 illustrates only one of the two sides of disk 10, the "lower" magnetic recording surface having substantially the same construction as the upper surface which is shown.

According to an important aspect of the invention, it has been discovered the start/stop lifetime of a carbon overcoat on a disc can be reliably estimated by combining resistance-to-erosion measurements, described below, with a measured lubricity property of the overcoat. The measured lubricity may be the static or dynamic coefficient of friction of the overcoat, or one of a number of properties related to the hydrophobicity of the overcoat, also as detailed below.

FIG. 2 is a schematic side view of a device 20 used in measuring the resistance to erosion of the carbon overcoat, in accordance with the invention. The device used in the method is a commercially available surface texturing machine conventionally used for removing surface irregularities on a disc and/or for producing a roughening or texturing a smooth disc surface, and whose operation is modified as described below. Device 20 includes a rotor 22 on which a disc, such as disc 24, is mounted for rotation about the disc axis, indicated by dotted line 26. The rotor is driven for rotation by a motor 28 whose speed can be adjusted for operation up to about 1,800 rpm.

A pair of rollers 30, 32 in the device are mounted on a frame 34 for rotatable contacting the confronting surface of a disc during operation of the device. Each roller, such as roller 30, is carried on an axle, such as axle 36, for rotation about its long axis when the roller is brought into contact with the spinning disc. Each axle is mounted on a track 38 in the frame for sliding movement thereon which moves the associated roller toward and away from the confronting side of a disc. The two roller axles are connected by a variable-tension spring 40, for applying a desired force of the rollers against the opposite sides of the disc. One preferred device of this type is commercially available form Exclusive Design Company (San Mateo, Calif.), Model No. 800 HDF-C.

According to one modified aspect of the operation of the device, the rollers are provided with an abrasive surface which is effective to wear away the overcoat during operation in a period of typically 5–15 minutes, at a selected force setting of the rollers, and selected disc speed. One preferred abrasive surface is a $0.3\mu$ particle size abrasive tape, such as tape No. 511904569 supplied by 3M Corp. (Minneapolis, Minn.).

The rollers are moved against the opposite disc surfaces with a force of typically between about 3–4 pounds, by adjustment of spring 40. The disc is then rotated at a selected speed, preferably about 1,800 rpm. According to another modified aspect of the operation of the device, the thickness of the overcoat is monitored, e.g., by visual inspection, or by a chromometer, to determine the time required to wear away a selected portion of the overcoat. Preferably the operation of the device is adjusted so that the overcoat is completely worn away in a period of several minutes. For, example, using the settings and abrasive material mentioned above, it has been found that a relatively soft carbon overcoat is worn away in about 2 minutes, as compared with a hard overcoat which is worn away in about 10 minutes.

Figure 3:
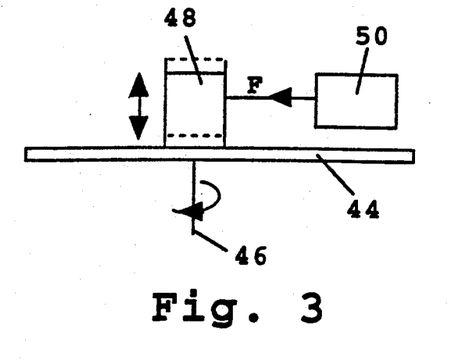
FIG. 3 is a side view, with components schematically represented, of a device for measuring the dynamic coefficient of friction of a carbon overcoat.

As mentioned above, the resistance-to-erosion measurements above are combined lubricity measurements to determine total start/stop lifetime of the disc overcoat. One measure of lubricity is the static or dynamic coefficient of friction of the overcoat. FIG. 3 is a schematic view of a device 42 used in measuring the dynamic coefficient of friction of a carbon overcoat surface on a disc, such as a disc 44. The device used in this test is a standard drag test for measuring the static and dynamic coefficient of a disc, such as the Model No. UTS-777 machine supplied by New Phase Technology (San Jose, Calif.).

Briefly, the device includes a motor-driven rotor, indicated at 46, for rotating the disc at a selected speed. A standard 9.5 g minicomposite read/write head 48 in the device is mounted for movement between positions of contact (solid lines) and non-contact (dotted lines) with the disc. This head, in turn, is coupled to a force transducer 50 which measures the force (in the direction of disc movement) applied to the head upon contact with the disc. The force measurement is used to determine the coefficient of friction. The dynamic coefficient of friction is measured at 1 rpm.

In one preferred testing method, the dynamic coefficient is measured, as above, both before and after a short drag period, typically 30 minutes. Here the 9.5 g read/write head is dragged for 30 minutes on an unlubricated disc rotating at about 300 rpm. Ideally, an overcoat will retain a relatively high lubricity (low coefficient of friction) after the 30-minute drag period.

The lubricity of the disc overcoat can also be measured in terms of the surface hydrophobicity of the overcoat. The correlation between greater hydrophobicity and greater lubricity appears to be due, at least in part, to the reduced degree of hydration which occurs on a hydrophobic disc surface. That is, reduced hydration of polar (hydrophilic) chemical groups, reduces the frictional drag at the overcoat surface.

Figure 4:
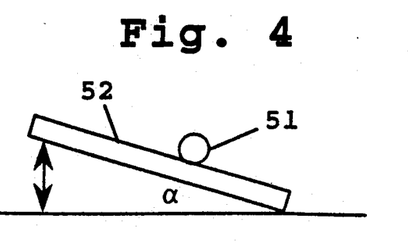
FIG. 4 illustrates a method for measuring bead angle on a carbon overcoat for determining hydrophobicity.

One simple measure of hydrophobicity is provided by a bead angle test, such as illustrated in FIG. 4. Here a drop of water 50 is placed on the upper surface of a disc, such as disc 52, and the disc is raised above horizontal to an angle $\alpha$ at which the bead first begins to glide on the surface, i.e., slide down the surface. Bead angles of between about 50 and 70 degrees, and preferably 60–70 degrees are typically observed. By comparison a conventional carbon overcoat formed according to prior-art methods has a bead angle of about 45 degrees or less and a lubricated (highly hydrophobic) overcoat has a bead angle of 90 degrees.

Chemical analysis of the surface chemical groups on the overcoat provides a more direct measure of hydrophobicity. One preferred method of surface chemical analysis is Electron Spectroscopy for Chemical Analysis (ESCA), which yields an electron density spectrum over a defined range of electron binding energies, where the type and density of characteristic chemical bonds on the surface can be identified by the position and areas of the peaks in the spectrum, respectively.

Figure 7A:
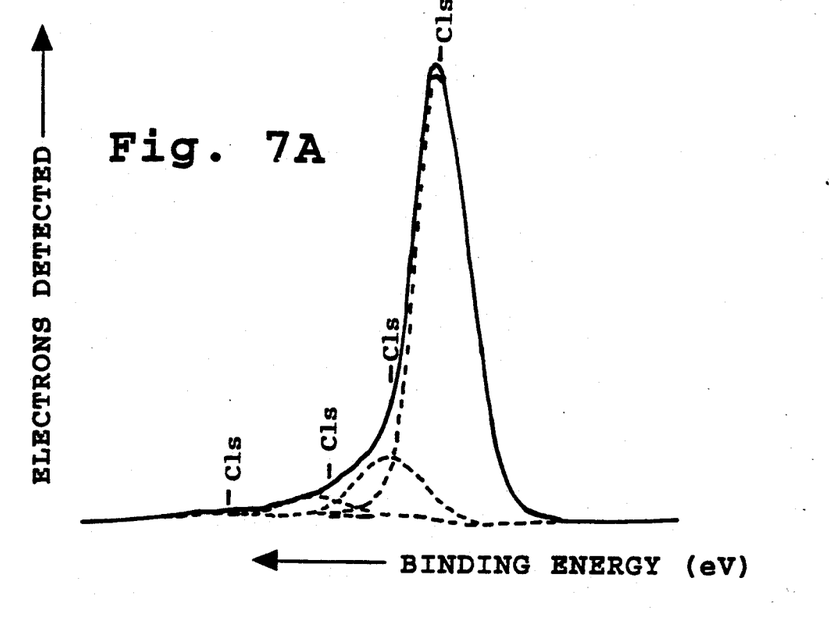
FIGS. 7A and 7B are ESCA spectra of carbon overcoats formed in the presence (7A) and absence (7B) of a hydrocarbon gas in an argon-containing atmosphere in a sputtering apparatus of the type shown in FIG. 5.
Figure 7B:
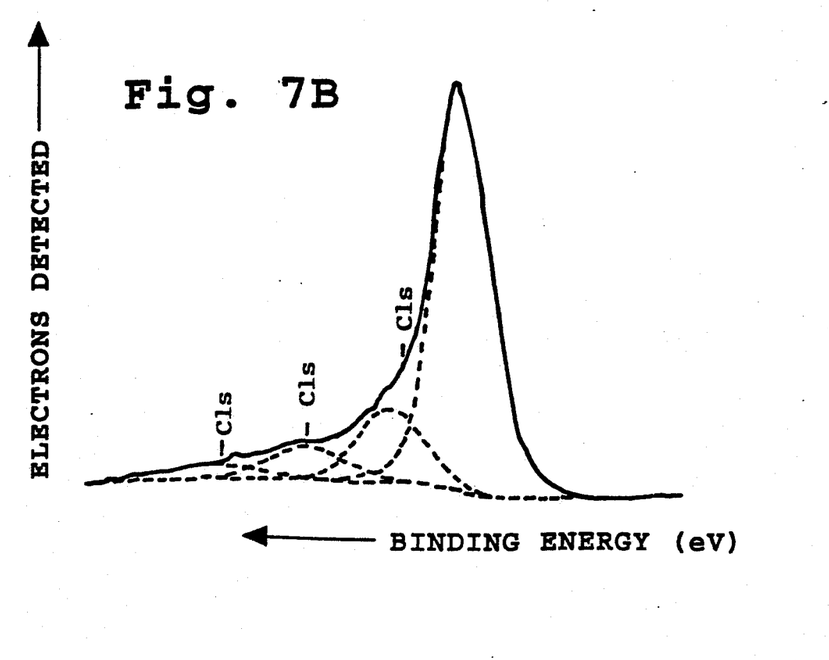

FIGS. 7A and 7B shows typical ESCA spectra for a carbon overcoat, over a spectral energy region from about 278–298 eV. The peaks are related to the 1s carbon electrons in C—C (284.38 eV), C—O (285.97 eV), C=O (287.81 eV), and O—C=O (289.83 eV) chemical groups, as indicated. As will be discussed below in Section III, the hydrophobicity in a preferred carbon overcoat is characterized by a ratio of C—C to C-oxygen containing bonds of at least about 4:1.

Also as well be described below, a disc having desired hydrophobicity properties is also characterized by a highly reflective surface and a bright gold color. These optical properties may therefore also be used to confirm that a disc has the desired hydrophobic surface properties.

In practicing the method of the invention, the resistance to erosion and lubricity of a disc are measured as detailed above. For example, resistance to erosion and dynamic coefficient of friction, and/or resistance to erosion and ESCA characteristics are measured. The measured values are then correlated with the same values determined for a surface overcoat with a known start/stop lifetime. Known lifetimes are measured conventionally by a standard start/stop test in which a read/write head is repeatedly brought into contact with the surface of a spinning disc, until the coefficient of friction of the disc increases above a selected threshold, e.g., 0.6.

By way of example, the actual start/stop lifetimes of a series of disc carbon overcoats having increasing resistance-to-erosion times between 5-10 minutes and, for each resistance to erosion time, having increasing coefficients of friction (after wear) of between 0.2-0.8 are determined. From these values, the expected lifetime of a carbon overcoat having a measured resistance to erosion and frictional coefficient can be determined.

It can be appreciated that the present invention allows the expected start/stop lifetime of a disc to be measured rapidly and with little wear on testing machinery. Thus, for example, a 10 minute resistance to erosion test, combined with measurements of the dynamic coefficient of friction (before and after 30 minutes of head drag) can now replace an extended test requiring several thousand disc/head contact cycles.

In addition to its use in disc quality control, the method is useful in evaluating the performance characteristics of an overcoat, for purposes of establishing the optimal operating parameters for forming a carbon overcoat in a sputtering method. This application of the present invention will be described below in Section III.

II. Sputtering Method

Figure 5:
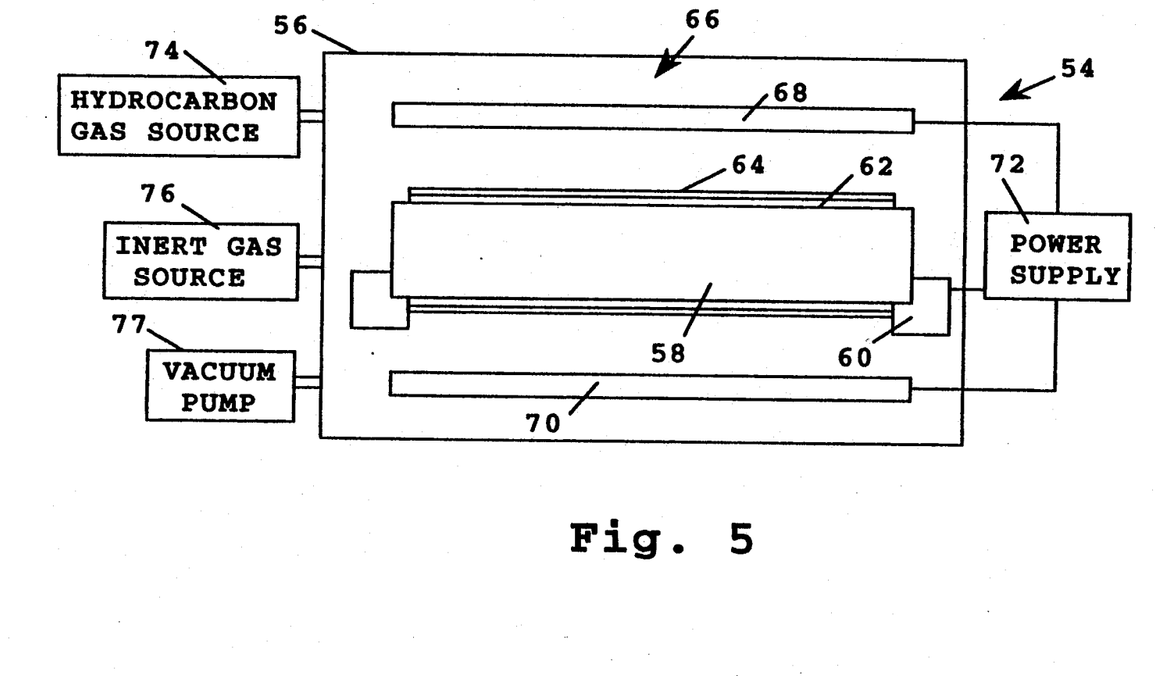
FIG. 5 is a schematic view of sputtering apparatus used in producing the disc shown in FIG. 1.

FIG. 5 is a schematic view of a sputtering apparatus 54 used in forming a carbon overcoat having desired hardness and lubricity characteristics. The apparatus generally includes a sputtering chamber 56 with one or more sputtering stations at which a thin-film layer is deposited on a substrate 58, typically a metal disc substrate as shown. The substrate is carried through the apparatus on a pallet 60, in a conveyor fashion, exposing each side of the disc successively to the sputtered material in the sputtering chambers.

Typically, the apparatus includes a first station at which a crystalline underlayer 62 is deposited, a second station at which a thin-film magnetic layer 64 is deposited, and a third station 66, shown in the figure, at which the final carbon overcoat is deposited. The sputtering conditions which are described below apply to station 66 in particular.

Station 66 houses a pair of carbon, i.e., graphite targets, 68, 70. The targets are connected to a power supply 72 in the apparatus to achieve a selected target voltage with respect to the disc, as shown. With a carbon target for use in forming a carbon overcoat, the voltage is typically adjustable between about 500 to 600 volts, giving a power level between about 0.8 and 4 kwatts.

The final pressure in the chamber during a sputtering operation is a selected pressure preferably between about $10^{-3}$ to $10^{-2}$ mBarr. The vacuum pressure is achieved with a conventional low-pressure vacuum pump 77.

A sputtering apparatus of the type just described is commercially available, such as from Circuits Processing Apparatus (Fremont, Calif.), Leybald Heraeus (Germany), VACTEK (Boulder, Colo.) or Materials Research Corp (Albany, N.Y.). These systems are all double-sided, in-line, high-throughput machines having two interlocking chambers for loading and unloading.

The carbon overcoat on the substrate is formed by sputtering under a low-pressure mixed-gas atmosphere. In accordance with the method, this atmosphere is composed of a selected amount of low-molecular weight hydrocarbon gas, preferably methane or ethane, and an inert gas, preferably argon. The percentage of these gases in the chamber is controlled by suitable valving of hydrocarbon and inert gas containers 74, 76, respectively. The percentage (mole percentage) of hydrocarbon gas in the chamber during overcoat formation is preferably at least about 20 percent, and preferably no higher than about 70 percent, with argon making up the remainder of the gas.

Figure 6:
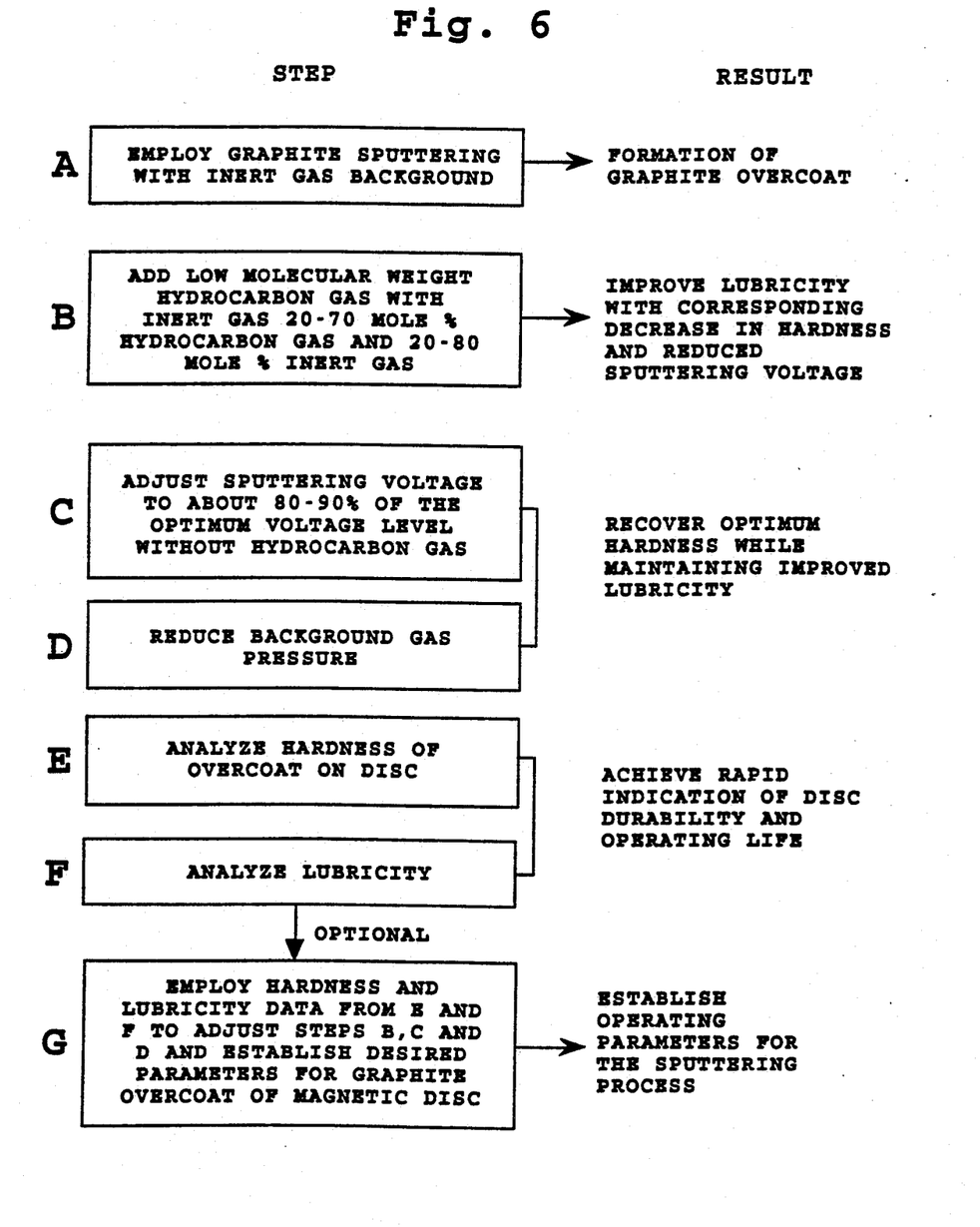
FIG. 6 is a block diagram of sequential steps which may be employed in various combinations to produce, in a thin-film magnetic medium, a carbon overcoat having desired hardness and lubricity properties.

FIG. 6 is a flow diagram showing how the testing method of the invention is used in optimizing sputtering conditions, to produce a carbon overcoat with selected hardness and lubricity properties. The first step shown is a conventional sputtering step in which a carbon overcoat is formed in a pure argon atmosphere, at a selected vacuum pressure. The voltage (and resulting power level) of the sputtering device is generally set close to the upper limits of the apparatus, e.g., about 580-600 volts. The voltage and rate of movement of the disc through the sputtering chamber are adjusted to produce a final overcoat thickness of between about 200-500 Å, and preferably close to 300 Å.

The carbon overcoat formed by sputtering in pure argon, as above, is tested for resistance to erosion and lubricity, as described in Section I. Generally the overcoat has good resistance to erosion but only moderate lubricity, as measured for example, by bead angle.

A carbon overcoat is next formed by sputtering in a low-pressure atmosphere containing a selected percentage of hydrocarbon gas, e.g., from 10-70 mole percent methane. The addition of low molecular weight hydrocarbon gas is initially made without any adjustment in sputtering voltage or in the chamber pressure. The carbon overcoat produced under these conditions shows increased lubricity, as measured both by coefficient of friction and bead angle, with increasing amounts of methane, up to about 30-50 mole percent methane. However, the resistance to erosion time decreases significantly with increasing methane concentrations.

According to an important feature of the sputtering method, it has been discovered that with suitable adjustments in sputtering voltage and gas pressure, both enhanced lubricity and high resistance to erosion times can be obtained.

Considering the voltage and power levels parameter, it is observed that voltage drops with increasing amounts of hydrocarbon gas in the chamber, presumably due to the lower impedance of the (ionized) hydrocarbon gas atmosphere. For example, a power supply setting which gives a sputtering voltage of about 600 volts in pure argon gives about 500 volts in 30-50% methane, at the same gas pressure.

The resistance to erosion of a disc overcoat prepared in methane:argon (50:50) at increasing voltage (and power levels) has been examined. Briefly, it was discovered that at a voltage of approximately 80-90% of the "pure argon" voltage—i.e., the optimal level employed for sputtering in a pure inert gas—that greater resistance to erosion was achieved, without loss of lubricity. The adjusted increase in voltage produces a corresponding increase in the power level for sputtering. Greater hardness (resistance to erosion) can be achieved at higher voltages.

It has also been discovered that additional increase in resistance to erosion can be achieved, also without loss of lubricity, by decreasing the chamber pressure of the hydrocarbon-containing gas mixture. It is noted here that this decrease in pressure tends to increase sputtering voltage, so that this parameter needs to be adjusted to an optimal level, as specified above. The final pressure in the chamber is preferably about 40% that in the chamber employing pure argon for sputtering. For example, the mixed gas pressure may be about $2-3 \times 10^{-3}$ mBarr. The resistance to erosion can be increased or reduced by lowering or raising the chamber pressure, respectively, from this level.

Once voltage, power level and gas pressure are adjusted for optimal hardness, at a given gas composition, the percentage of hydrocarbon gas may be further adjusted to enhance lubricity. By testing resistance to erosion at the same time, the voltage, power level and gas pressure conditions can also be systematically refined to maintain or increase overcoat hardness, without loss of lubricity.

It will be appreciated from above how the testing method of the invention facilitates the selection of optimal sputtering conditions, for achieving desired hardness and lubricity properties. The resistance-to-erosion test, by providing a quantitative measure of overcoat hardness, allows sputtering conditions to be systematically controlled to produce a desired hardness. At the same time, by selecting sputtering conditions which also produce good lubricity, the method assures a disc with good overcoat durability and long start/stop lifetime.

III. Overcoat Surface Properties

The testing and sputtering methods described have been employed to produce a thin-film medium carbon overcoat having the following thickness, and improved hardness, and lubricity characteristics.

Thickness. The carbon overcoat has a thickness less than about 500 Å and preferably about 300 Å, when used as a protective coating in a thin-film magnetic recording medium. For other applications, for example, where the overcoat is used to provide a protective lubricating surface for plastic or metal mechanical parts, the film thickness may be greater (or less) than this specified thickness. The thickness of the overcoat may be controlled, as above, by suitable adjustment in the time-of-travel of the article to be coated through the carbon sputtering station.

Resistance to Erosion. Resistance-to-erosion, as defined herein, is measured in terms of the time required to wear away a 300 Å overcoat on a disc, when a $0.3\mu$ abrasive tape is applied to the surface of the disc with a force of about 3.5 pounds, and the disc is rotated at 1,800 rpm. These test conditions, although arbitrarily selected, are useful for making quantitative comparisons of overcoat hardness which can be used both for optimizing sputtering conditions and for determining start/stop lifetimes, as above.

The carbon overcoat produced in accordance with above methods has a resistance-to-erosion time of at least about 8 minutes, with erosion times up to 10 minutes being achievable. An overcoat having this degree of hardness, as well as high lubricity, is generally well suited for conventional hard-disc computer storage applications. However, applications which favor softer carbon overcoats are also contemplated.

Coefficient of Friction. The coefficient of friction, as defined herein, is the coefficient of friction measured with a standard read/write head. The dynamic coefficient is measured at a disc rotating at a speed of 1 rpm, and the static coefficient, from a stationary disc position.

The carbon overcoat has a static and dynamic coefficient of between about 0.2 and 0.3. To measure static and dynamic coefficient of friction after extended start/cycles, a disc coated with fluorocarbon lubricant was subjected to 30,000, 60,000, and 90,000 start/stop cycles, and tested for static coefficient. Even after 90,000 start/stop cycles, the static coefficient, as measured in several disc, was between 0.2 to 0.45.

Similarly, the disc showed little or not increase in dynamic coefficient of friction after a 30-minute head drag period, at a disc speed of 300 rpm.

By contrast, a disc overcoat formed in accordance with prior art sputtering methods showed gave static coefficient of friction values of to 0.6–0.7 after 20,000 start/stop cycles.

Hydrophobicity: Bead Test. The bead angle at which a bead (e.g., a 10–20 $\mu$l bead) of distilled water first begins to glide on the overcoat surface is between about 50 and 70 degrees and preferably between 60–70 degrees, as measured from the horizontal.

Hydrophobicity: Carbon Bond Ratio. FIGS. 7A and 7B are plots of the ESCA spectra of carbon overcoats prepared in the presence (7A) and absence (7B) of hydrocarbon gas in the sputtering chamber. The spectra were broken down into peak components by a standard curve fitting program, and the calculated peaks, representing C—C bonds (284.38 eV), alcohol C—O (285.97 eV), ketone C=O (287.81 eV) and acid and aldehyde O—C=O groups (289.83 eV), are shown in dotted lines in the two figures. The percent of each bond type on the surface, calculated by area under the curve, is given in Table I for an overcoat formed in either pure argon atmosphere (third column) and in a methane/argon atmosphere (fourth column).

TABLE I

| Energy | Bond | Percent (argon) | Percent (argon/methane) |
|---|---|---|---|
| 284.58 | C—C | 71.5 | 81.7 |
| 285.79 | C—O | 14.8 | 12.9 |
| 287.42 | C=O | 8.7 | 4.2 |
| 289.56 | O—C=O | 5.0 | 1.2 |

As seen, the overcoat formed in an argon/hydrocarbon gas has a ratio of carbon-carbon (hydrophobic) bonds to carbon-oxygen (hydrophilic) bonds of greater than 4:1, and substantially higher than an overcoat produced by carbon sputtering in a pure inert gas environment.

Optical Properties. The carbon overcoat formed in accordance with the sputtering and test methods described herein is also characterized by high reflectivity. Although this property has not been quantitated, initial visual observations indicate that the disc overcoat is substantially more reflective than carbon overcoats in commercially available discs.

The present carbon overcoat also has a distinctive bright gold color. This color is easily distinguished from the typically grey to brown color of known disc overcoats. It is assumed that the high reflectivity and/or bright gold color of the overcoat are related to the hydrophobicity of the disc and therefore may be diagnostic of a disc overcoat having desired hydrophobicity characteristics.

Start-Stop Lifetime. As defined herein, "start/stop lifetime" is defined as the number of start/stop cycles which a lubricated disc overcoat may be subjected to without an increase in static or dynamic coefficient, beyond an acceptable specified value, e.g., 0.5–0.7. The start/stop lifetime is measured conventionally be measuring static coefficient of a lubricated disc before and after an increasing number of start/stop cycles, e.g., 20,000 and 10,000 increments thereof.

By such standard start/stop lifetime testing, the present overcoat (coated with a fluorocarbon lubricant) gave up to 90,000 start/stop cycles without significant increase in static coefficient, as mentioned above. This compares with the overcoat wear properties of commercially available discs which show significant increases in static coefficient of friction after 20,000–30,000 start/stop cycles.

Although the invention has been described with respect to preferred test methods, and their application to producing thin-film disc carbon overcoats by DC magnetron sputtering, it will be appreciated that various changes and modifications may be made without departing from the invention.

It is claimed:

1. A method of evaluating the expected start-stop lifetime of a thin-film magnetic disc formed by sputtering a carbon-containing overcoat on a thin-film substrate, comprising
    (a) measuring the resistance to erosion of the overcoat by (a) placing against the disc, a roller covered with an abrasive tape and oriented to rotate with disc rotation, (b) rotating the disc, and (c) with the roller pressed against the overcoat, measuring the overcoat removal time required to remove a selected portion of the overcoat;
    (b) measuring the lubricity of the overcoat; and
    (c) correlating the measured resistance to erosion and lubricity with the resistance to erosion and lubricity measured in discs with known start-stop lifetimes.

2. The method of claim 1, wherein the resistance to erosion is measured by rotating the disc at a speed of about 1,800 rpm, under conditions in which the hardest disc overcoats can be substantially worn away within at most about 15 minutes.

3. The method of claim 1, wherein said lubricity measuring includes measuring the coefficient of friction of a read/write head in contact with disc.

4. The method of claim 3, wherein said lubricity measuring includes measuring the coefficient of friction of a read/write head on the disc, after a 30-minute head drag period at a disc speed of 300 rpm.

5. The method of claim 4, wherein the coefficient of friction is in the range between about 0.2–0.5 before and after such head-drag period.

6. The method of claim 1, wherein said lubricity measuring includes measuring the hydrophobicity of the overcoat.

7. The method of claim 6, wherein said hydrophobicity measuring includes measuring the angle from horizontal at which a bead of water placed on the disc begins to glide.

8. The method of claim 6, wherein said hydrophobicity measuring includes measuring the ratio of exposed carbon:oxygen-containing groups on the overcoat surface.

9. The method of claim 8, wherein said ratio is greater than about 4:1.

10. The method of claim 6, wherein said hydrophobicity measuring includes measuring the reflectivity of the disc.

11. The method of claim 6, wherein said hydrophobicity measuring includes observing a bright gold color.

12. The method of claim 1, for use in optimizing sputtering conditions used in achieving a desired balance between hardness and lubricity in the overcoat of a thin-film magnetic disc, in forming a graphite overcoat on a substrate by a sputtering process carried out under a low-pressure, inert-gas atmosphere in a closed chamber with a sputtering power level being developed for initiating sputtering, which further includes adjusting the composition of the gas present at low pressure during sputtering to increase the lubricity of the overcoat, and varying the sputtering voltage and pressure in the chamber to achieve a desired degree of hardness.

13. The method of claim 12, wherein the composition of the gas present during sputtering contains an inert gas and between about 20–70 mole percent low molecular weight hydrocarbon, and said adjusting includes varying the relative mole ratios of the inert gas and hydrocarbon.

14. A method of establishing gas pressure and sputtering voltage conditions for sputtering a graphite overcoat on a substrate to produce a selected start-stop lifetime in a disc formed by said sputtering, said method comprising
    measuring resistance to erosion of the graphite overcoat by (a) placing against the disc, a roller covered with an abrasive tape and oriented by rotate with disc rotation, (b) rotating the disc, and (c) with the roller pressed against the overcoat, measuring the overcoat removal time required to remove a selected portion of the overcoat, measuring the lubricity of the graphite overcoat, and
    adjusting said sputtering conditions to produce a selected resistance to erosion and lubricity corresponding to such selected start-stop lifetime.

15. The method of claim 14, wherein the resistance to erosion is measured by rotating the disc at a speed of about 1,800 rpm, under conditions in which the hardest disc overcoats can be substantially worn away within at most about 15 minutes.

16. The method of claim 14, wherein said lubricity measuring includes measuring at least one of the following surface characteristics: (a) the static coefficient of friction of a read/write head in contact with disc, (b) the dynamic coefficient of friction of a read/write head in contact with disc, (c) the angle from horizontal at which a bead of water placed on the disc begins to glide, (d) the ratio of exposed carbon-carbon to carbon-oxygen-containing groups on the overcoat surface, (e) the surface reflectivity of the disc, and (f), color of the disc.

17. The method of claim 14, which further includes adjusting the sputtering voltage in a sputtering apparatus, in response to said measuring of resistance to erosion, to produce a selected hardness in the overcoat.

18. The method of claim 14, which further adjusting the pressure in a sputtering apparatus, in response to said measuring of resistance to erosion, to produce a selected hardness in the overcoat.

19. The method of claim 14, which further adjusting the percent of hydrocarbon gas in an argon/hydrocarbon gas mixture in a sputtering apparatus, in response to said measuring of lubricity, to produce a selected lubricity in the overcoat.

20. The method of claim 19, which further adjusting the sputtering voltage and chamber pressure in a sputtering apparatus, in response to said measuring of resistance to erosion, to produce a selected hardness and lubricity in the overcoat.

* * * * *